(12) United States Patent
Luo et al.

(10) Patent No.: US 10,898,541 B2
(45) Date of Patent: Jan. 26, 2021

(54) USE OF ANTIMICOBIAL PEPTIDES FOR TREATMENT OF INFECTION

(71) Applicant: HUNAN UNIVERSITY OF SCIENCE AND ENGINEERING, Hunan (CN)

(72) Inventors: Xiaofang Luo, Hunan (CN); Zuodong Qin, Hunan (CN); Fulin He, Hunan (CN); Xiaoping Ouyang, Hunan (CN); Zhizhang Li, Hunan (CN); Changjian Li, Hunan (CN); Qianrui Peng, Hunan (CN); Zhesheng Chen, Hunan (CN)

(73) Assignee: HUNAN UNIVERSITY OF SCIENCE AND ENGINEERING, Yongzhou (CN)

(*) Notice: Subject to any disclaimer, the term of this patent is extended or adjusted under 35 U.S.C. 154(b) by 0 days.

(21) Appl. No.: 16/790,669

(22) Filed: Feb. 13, 2020

(65) Prior Publication Data

US 2020/0197479 A1   Jun. 25, 2020

Related U.S. Application Data

(60) Division of application No. 16/407,132, filed on May 8, 2019, now Pat. No. 10,603,350, which is a continuation of application No. PCT/CN2017/109799, filed on Nov. 7, 2017.

(30) Foreign Application Priority Data

Nov. 9, 2016 (CN) .......................... 2016 1 0983926

(51) Int. Cl.
| | | |
|---|---|---|
| *A61P 31/04* | (2006.01) | |
| *A61K 38/10* | (2006.01) | |
| *A61P 35/00* | (2006.01) | |
| *A23K 20/147* | (2016.01) | |
| *A23L 33/18* | (2016.01) | |
| *A61P 31/10* | (2006.01) | |

(52) U.S. Cl.
CPC ............ *A61K 38/10* (2013.01); *A23K 20/147* (2016.05); *A23L 33/18* (2016.08); *A61P 31/04* (2018.01); *A61P 31/10* (2018.01); *A61P 35/00* (2018.01)

(58) Field of Classification Search
None
See application file for complete search history.

(56) References Cited

U.S. PATENT DOCUMENTS

2012/0237501 A1*  9/2012  Wang ..................... A61K 38/04
                                                            424/130.1

* cited by examiner

*Primary Examiner* — Fred H Reynolds
(74) *Attorney, Agent, or Firm* — Wayne & Ken, LLC; Tony Hom

(57) ABSTRACT

Disclosed are antimicrobial peptides capable of inhibiting and killing multiple drug-resistant bacteria, including XH-12C, XH-12B and XH-12A. The application further provides uses of the antimicrobial peptides in the preparation of a drug for inhibiting and/or killing fungi, Gram-positive bacteria, Gram-negative bacteria and drug-resistant bacteria and in the manufacture of medical carriers.

2 Claims, 3 Drawing Sheets

Specification includes a Sequence Listing.

USE OF ANTIMICROBIAL PEPTIDES FOR TREATMENT OF INFECTION

CROSS-REFERENCE TO RELATED APPLICATION

This application is a divisional application of U.S. patent application Ser. No. 16/407,132, which is a continuation of International Patent Application No. PCT/CN2017/109799, filed on Nov. 7, 2017, claiming the benefit of priority from Chinese Application No. 201610983926.6, filed on Nov. 9, 2016. The contents of the aforementioned applications, including any intervening amendments thereto, are incorporated herein by reference in its entirety.

REFERENCE TO AN ELECTRONIC SEQUENCE LISTING

The contents of the electronic sequence listing (Untitled_ST25.txt; Size: 1,000 bytes; and Date of Creation: Mar. 14, 2020) is herein incorporated by reference in its entirety.

TECHNICAL FIELD

The application relates to antimicrobial peptides, and more particularly to a use of an antimicrobial peptide for treating an infection.

BACKGROUND

The misuse of antibiotics results in a high level of drug resistance and multidrug resistance (MDR) in pathogenic microorganisms, which has become a worldwide problem. Recently, the "superbugs" with MDR have spread rapidly around the world, seriously threatening human life and health. Studies have shown that pathogenic bacteria can obtain MDR through some mechanisms such as horizontal gene transfer to resist a variety of antibiotics used clinically. The modification of existing antibiotics and development of new antibiotics are conducted to overcome the challenges from "superbugs", in addition to which, alternatives of antibiotics are expected to be developed to alleviate the international health security crisis caused by the "superbugs".

SUMMARY

The present invention provides an antimicrobial peptide capable of inhibiting and killing multiple drug-resistant bacteria and uses thereof.

An antimicrobial peptide capable of inhibiting and killing multiple drug-resistant bacteria of the application is any one peptide selected from the group consisting of:

```
XH-12C:
Phe-Phe-Arg-Lys-Val-Leu-Lys-Leu-Ile-Arg-Lys-Ile-
Trp-Arg shown as SEQ ID NO. 1;

XH-12B:
Phe-Phe-Arg-Lys-Val-Leu-Lys-Leu-Ile-Arg-Lys-Ile-
Phe shown as SEQ ID NO. 2;
and XH-12A:
Phe-Phe-Arg-Lys-Val-Leu-Lys-Leu-Ile-Arg-Lys-Ile
shown as SEQ ID NO. 3.
```

The application further discloses a method of treating an infection in a patient in need thereof, comprising:

administering XH-12C, XH-12B, XH-12A or a combination thereof to the patient; wherein the infection is caused by a fungus, a Gram-positive bacterium, a Gram-negative bacterium or a drug-resistant bacterium.

In an embodiment, the fungus is *Candida albicans*; the Gram-positive bacterium is *Staphylococcus aureus* and *Listeria monocytogenes*; the Gram-negative bacterium is *Escherichia coli*; and the drug-resistant bacterium is selected from the group consisting of drug-resistant *Staphylococcus aureus*, drug-resistant *Acinetobacter baumannii*, drug-resistant *Klebsiella pneumoniae*, drug-resistant *Enterobacter sakazakii*, drug-resistant *Salmonella gallinarum*, drug-resistant *Streptococcus agalactiae*, drug-resistant *Enterococcus faecalis* or drug-resistant *Riemerella anatipestifer*.

The application also provides a use of the antimicrobial peptide in the preparation of a drug for treating a cancer.

In an embodiment, the cancer comprises cancer cells selected from H460, KB-3-1 or drug-resistant cancer cells MX20, KB-C2 or KB-CV60.

The invention further provides a use of the antimicrobial peptide in the manufacture of a medical carrier.

In an embodiment, the drug comprises at least one of XH-12C, XH-12B, and XH-12A. In an embodiment, the drug is mixed with at least one pharmaceutically acceptable carrier or additive.

In an embodiment, the antimicrobial peptide is applied in any one of human drug (for antimicrobial, anticancer and burn treatment), veterinary drug, food additive, feed additive and daily chemical product.

The antimicrobial peptide of the present invention is prepared by a BOC method in the existing solid phase peptide synthesis. The BOC method includes:

(1) synthesis of resin
Peptide acid Merrifield resin and PAM resin;
Peptide carboxamide MBHA resin;
(2) synthesis of a peptide chain
2.1 coupling of amino acids
2.2 removal of an N-terminal Boc group
removing the N-terminal Boc protective group with TFA before HF cleavage, where the N-terminal Boc group is artificially cleaved by washing with a solution of TFA and DCM in a ratio of 1:1 at room temperature for 15 minutes;
(3) Cleavage
3.1 treatment of resin before the cleavage
completely washing and drying the resin before the cleavage; where the resin may be treated as follows in some special cases:

A) cleavage of a dinitrophenyl (DNP) protective group of His swelling the resin with a minimum volume of DMF; treating the resin with 20 mol of thiophenol for 1-2 hours; transferring the resin to a bonding glass funnel; and washing the resin frequently with a HF solution, or before treatment with TFMSA, washing the resin with DMF, methanol and cold ethyl ether;

B) deformylation of a Trp-containing polypeptide resin
adding a solution of piperidine and DMF at a volume ratio of 1:10 to a round-bottom flask; cooling the solution in an ice bath; introducing the polypeptide resin (1 g/mL) to the solution followed by stirring at 0° C. for 2 hours for reaction; washing the resin twice with DMF (5 times the volume of the resin), twice with DCM and twice with MeOH; and drying the resin for at least 4 hours under high vacuum before the cleavage with HF;

3.2 UD cleavage standard HF-cleaving method (0.2 mmol)

A) adding the polypeptide resin, a polytetrafluoroethylene tube and a purificant mixture to a reaction vessel, where a purificant mixture of HF, anisole, DMS and p-tolyl mercaptan in a ratio of 10:1:1:0.2 is used to treat a polypeptide with Cys, while a polypeptide without Cys is treated with a purificant mixture of HF, DMS and anisole in a ratio of 10:1:1;

B) screwing a cap tightly and cooling the reaction mixture in an icy pure methanol for at least 5 minutes;

C) distilling 10 mL of HF to a bottle following the instructions of the manufacture, since it may take more than 2 hours for cleavage of an Arg (Tos)-containing polypeptide;

D) at the end of the reaction, evaporating HF and DMS by nitrogen steam;

E) absorbing the cleaved polypeptide from the resin with TFA;

F) collecting the resin by filtration under vacuum; washing the resin twice with TFA followed by filtration to obtain a filtrate; and adding cold ethyl ether (8-10 times the volume of the filtrate) to the filtrate; where in some cases, there is a need to evaporate most of the TFA to obtain a precipitate of a crude product;

3.3 post-processing of the cleavage

A) precipitation collecting the precipitated peptide by filtration with a hard filter paper in a Hirsch funnel under vacuum; washing the precipitated peptide with cold ethyl ether; and dissolving the precipitated peptide in an appropriate buffer solution followed by lyophilization;

B) centrifugation adding a small volume of tert-butyl methyl ether to the lyophilized product followed by grinding until a suspended substance is produced; transferring the suspended substance to a clean centrifuge tube followed by hermetic centrifugation, where an automatic centrifuge is necessary; pouring the ether carefully out of the tube and washing the precipitate repeatedly with the ether; and dissolving the precipitate in an appropriate buffer solution followed by lyophilization;

C) after the water-soluble peptide is precipitated, adding water to the precipitate to produce a mixture; and transferring the mixture to a separatory funnel to which a small amount of ethanol may be added to promote dissolution;

D) shaking the sealed funnel thoroughly to disperse the mixture followed by standing for separation; and collecting the lower-layer liquid (water);

E) adding a small amount of water to the funnel; repeating the process of shaking-standing-separation three times; collecting the lower-layer liquid to a clean flask and removing the upper-layer liquid; and transferring the lower-layer liquid to the funnel;

F) adding a small amount of a freshly prepared diethyl ether; repeating the process of shaking-standing-separation two to three times, where the ether layer is removed each time and the water layer is recycled to the funnel; and after that, collecting the water layer to a clean flask followed by lyophilization to produce the antimicrobial peptide.

A use of the antimicrobial peptide of the invention in the preparation of, for example a drug for treating the infection caused by Gram-positive bacteria such as *Staphylococcus aureus* and *Listeria monocytogenes* or Gram-negative bacteria such as *Escherichia coli*, particularly in the preparation of a human drug or a veterinary drug for killing and inhibiting *Staphylococcus aureus, Listeria monocytogenes* and/or *Escherichia coli*.

The drug may comprise one or more of the antimicrobial peptides disclosed herein.

The drug may further comprise one or more pharmaceutically acceptable carriers or additives, such as an active enzyme for promoting enzymatic hydrolysis, or an activator for enhancing dispersion.

The dosage and use conditions of the antimicrobial peptide of the invention in the above use methods can be determined by the methods known in the art.

It has been experimentally demonstrated that the antimicrobial peptide of the present invention plays a significant role in inhibiting and killing Gram-positive bacteria, particularly *Staphylococcus aureus* and *Listeria monocytogenes*, Gram-negative bacteria, particularly *Escherichia coli*, or fungi, particularly *Candida albicans*. In addition, the application also has a significant effect on multiple drug-resistant bacteria, ordinary cancer cells and drug-resistant cancer cells.

In summary, the antimicrobial peptide of the invention has a broad-spectrum antimicrobial activity, a low hemolytic activity and an anti-cancer activity, and particularly provides a desirable therapeutic effect on drug-resistant bacteria and drug-resistant cancer cells. Therefore, the present invention is promising in the applications of medicines, food and daily chemical products.

BRIEF DESCRIPTION OF THE DRAWINGS

The embodiments of the invention are further described in detail below with reference to the accompanying drawings.

DETAILED DESCRIPTION OF EMBODIMENTS

Figure 1A:
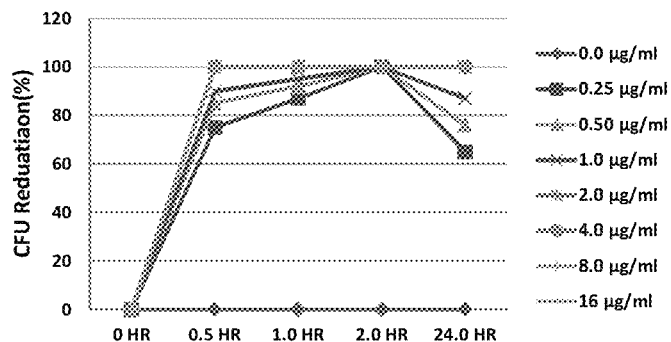
FIGS. 1A-C show the effect of the antimicrobial peptide XH-12A on killing *Staphylococcus aureus* (A), *Listeria monocytogenes* (B), and *Escherichia coli* (C).

The invention will be further illustrated below with reference to the embodiments, but are not limited thereto.

Example 1 Evaluation of Minimum Inhibitory Concentration (MIC) Using Micro-Broth Dilution Method (A) Preparation of Antimicrobial Drug and Medium The antimicrobial drug and the medium were prepared according to a constant broth dilution method.

Concentration range of the antimicrobial drug for susceptibility test includes boundary points of the resistant, intermediate and susceptible values according to the NCCLS Antimicrobial Susceptibility Test Operating Standard.

A Mueller-Hinton (MH) broth at pH of 7.2-7.4 recommended by NCCLS was used herein as the medium in which aerobic bacteria and facultative anaerobic bacteria grew well.

Preparation of Inoculum 3-5 colonies to be examined of similar morphology were picked up by an inoculating loop, inoculated in 4-5 mL of casein hydrolysate (MH) broth and cultured at 35° C. for 2-6 hours. After the enrichment, the bacterial suspension at the logarithmic phase was adjusted with normal saline or MEI broth to a concentration of 0.5 McFarland standard, i.e., about $1\times10^8$-$2\times10^8$ CFU/mL.

B) Preparation of MIC Plate

Under sterile conditions, different concentrations of the antimicrobial drug solutions obtained by multiple dilution were respectively added to a sterilized 96-well polystyrene plate, where the $1^{st}$ to the $11^{th}$ wells were added with the drug solution at 10 μL per well and the $12^{th}$ well free of drug solution was used as the growth control. Then the 96-well plate was lyophilized, sealed and stored at −20° C. for use.

C) Preparation of Inoculum

A bacterial suspension prepared by a growth method or a direct bacterial suspension method and having a concentration equivalent to 0.5 McFarland standard was diluted with MH broth in a ratio of 1:1,000 and added to the 96-well plate at 100 μL per well. The plate was sealed and incubated at 35° C. in an ordinary air incubator for 16-20 hours for assessment, where drug concentrations of the $1^{st}$ to the $11^{th}$ wells were 128, 64, 32, 16, 8, 4, 2, 1, 0.5, 0.25 and 0.125 μg/mL, respectively.

D) Results

The results were assessed as follows. The minimum concentration at which the drug completely inhibits the bacterial growth in the wells was the minimum inhibitory concentration (MIC). The test was useful only when the bacteria grew significantly in the positive control well (i.e., no antibiotics). When a single drift occurred in the micro-broth dilution method, the highest concentration at which the drug inhibited the bacterial growth was recorded.

The results were shown in Table 1.

TABLE 1

| Peptides | Staphylococcus aureus | Listeria monocytogenes | Escherichia coli |
| --- | --- | --- | --- |
| XH-12A | 4 μg/mL | 4 μg/mL | 32 μg/mL |
| XH-12B | 16 μg/mL | 16 μg/mL | 64 μg/mL |
| XH-12C | 16 μg/mL | 8 μg/mL | 32 μg/mL |

*Staphylococcus aureus*, *Listeria monocytogenes* and *Escherichia coli* used in this test were ATCC25922, ATCC19115 and ATCC29213, respectively.

Example 2 Minimum Bactericidal Concentration (MBC) Test

The minimum bactericidal concentration referred to a minimum concentration required for killing 99.9% (reduced by 3 orders of magnitude) of the test microorganisms.

Figure 1B:
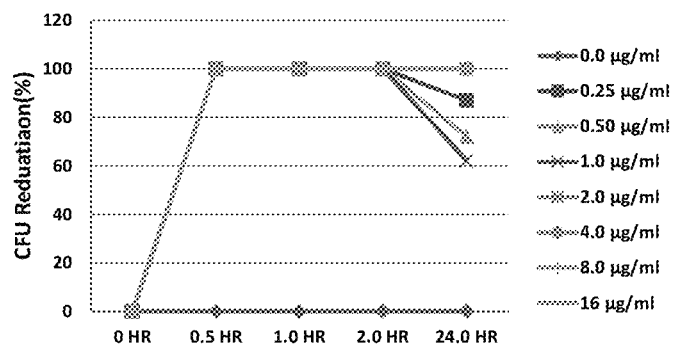
Figure 1C:
Figure 2A:
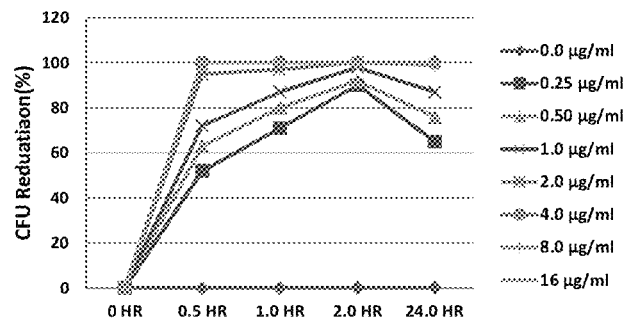
FIGS. 2A-C show the effect of the antimicrobial peptide XH-12B on killing *Staphylococcus aureus* (A), *Listeria monocytogenes* (B), and *Escherichia coli* (C).
Figure 2B:
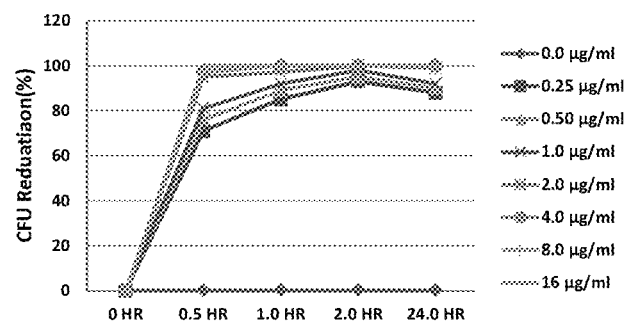
Figure 2C:
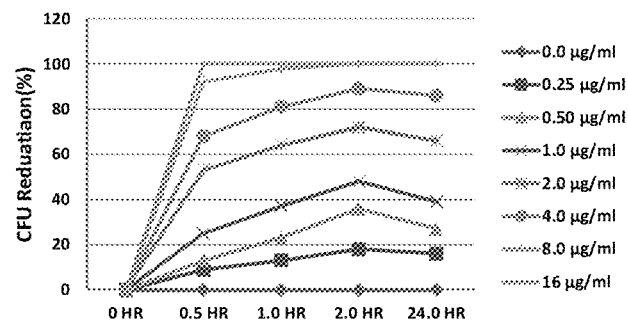
Figure 3A:
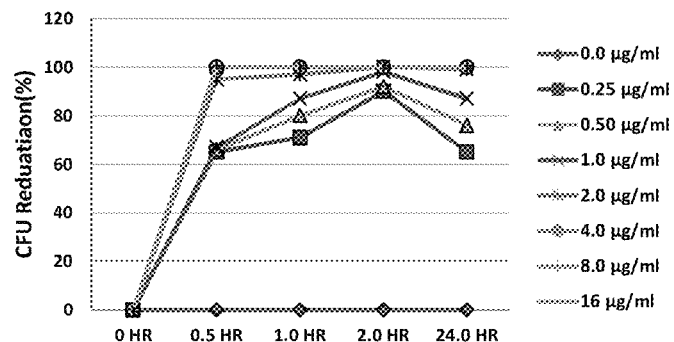
FIGS. 3A-C show the effect of the antimicrobial peptide XH-12C on killing *Staphylococcus aureus* (A), *Listeria monocytogenes* (B), and *Escherichia coli* (C).
Figure 3B:
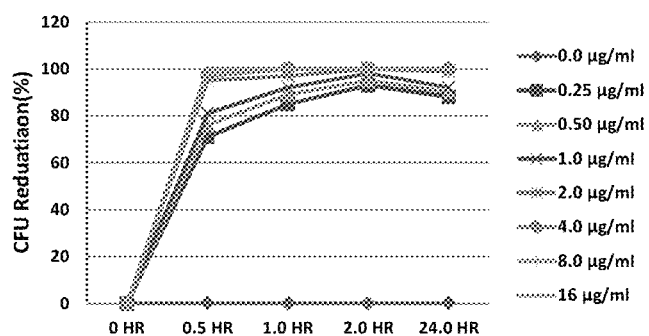
Figure 3C:
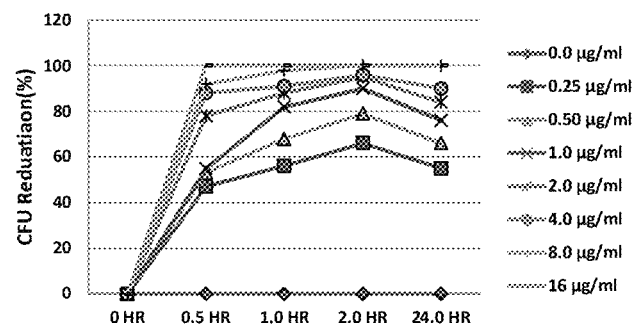

The determination of the minimum bactericidal concentration using a doubling dilution method was performed by halving the drug concentrations in order. For example, when the minimum bactericidal concentration (MBC) was determined in a certain row/column of a 96-well plate, each well was added with 10 μL of different concentrations of the drug solution to provide the first well with a final drug concentration of 128 μg/mL, the second well with a final drug concentration of 64 μg/mL and the third well with a final drug concentration of 32 μg/mL, and so on. A lowest drug concentration at which no viable cells were observed was the MBC. The results were shown in FIGS. 1A-1C, 2A-2C and 3A-3C.

In FIGS. 1A-1C, 2A-2C and 3A-3C, HR referred to hour; concentration was presented by μg/mL; and CFU reduction % referred to percentage for colony reduction.

*Staphylococcus aureus*, *Listeria monocytogenes* and *Escherichia coli* used in this test were ATCC25922, ATCC19115 and ATCC29213, respectively.

Example 3 Determination of Inhibitory Activity and Minimum Inhibitory Concentration (MIC) Against Multidrug-Resistant Bacteria A doubling dilution method was used to determine the minimum inhibitory concentration. The test strains were multidrug-resistant *Acinetobacter baumannii*, *Klebsiella pneumonia*, *Staphylococcus aureus*, *Enterobacter sakazakii*, *Salmonella gallinarum*, *Streptococcus agalactiae*, *Enterococcus faecalis* and *Riemerella anatipestifer*. Each of the strains was inoculated to an MEI solid medium and incubated invertedly at 37° C. in an incubator. After the colonies appeared, the single colony was transferred to an MEI liquid medium by an inoculating loop and incubated at 37° C. under shaking in an incubator to the logarithmic growth phase. Then $OD_{600}$ of the bacterial liquid was measured by an ultraviolet spectrophotometer, and the concentration of the bacterial liquid was calculated according to 1 $OD_{600}$=1× $10^9$ CFU/mL. After that, the bacterial liquid was diluted with the MH medium to $2\times10^5$ CFU/mL. 90 μL of the diluted bacterial liquid and 10 μL of a peptide solution were added and mixed uniformly in each well of a 96-well plate, incubated at 37° C. for 18 hours and measured by a microplate reader for $OD_{600}$. The minimum concentration of a sample to inhibit the bacterial growth was the minimum inhibitory concentration (MIC) of the sample. The experiment was repeated 3 times and the results were averaged and shown in Tables 2-3.

TABLE 2

Minimum inhibitory concentration of antimicrobial peptides against multi drug-resistant bacteria in human

|  | multidrug-resistant Staphylococcus aureus | multidrug-resistant Acinetobacter baumannii | multidrug-resistant Klebsiella pneumoniae |
| --- | --- | --- | --- |
| XH-12C | 4 μg/mL | 4 μg/mL | 4 μg/mL |
| XH-12B | 4 μg/mL | 8 μg/mL | 4 μg/mL |
| XH-12A | 4 μg/mL | 8 μg/mL | 8 μg/mL |

TABLE 3

Minimum inhibitory concentration of antimicrobial peptides against multidrug-resistant bacteria in animals

| | Enterobacter sakazakii | Salmonella gallinarum | Streptococcus agalactiae | Enterococcus faecalis | Riemerella anatipestifer |
|---|---|---|---|---|---|
| XH-12C | 300 µg/mL | 300 µg/mL | 50 µg/mL | 200 µg/mL | 300 µg/mL |
| XH-12B | 300 µg/mL | 300 µg/mL | 50 µg/mL | 50 µg/mL | 300 µg/mL |
| XH-12A | 250 µg/mL | 300 µg/mL | 50 µg/mL | 50 µg/mL | 300 µg/mL |

The experimental results showed that the above antimicrobial peptides had inhibitory activities against multidrug-resistant bacteria in both human and animals.

Example 4 Determination of Inhibitory Activity and Minimum Inhibitory Concentration (IC) Against Fungi According to the M27-A protocol of NCCLS, the antimicrobial peptide was diluted by doubling dilution and 100 µL of the diluted peptide was added to a 96-well plate followed by adding of 100 µL of a suspension at $0.5$-$2.5 \times 10^3$ Candida albicans/mL and cultured at 37° C. for 48 hours. The minimum peptide concentration at which no bacterial growth was observed was the MIC of the antimicrobial peptide against Candida albicans. The experiment was repeated 3 times and the results were averaged and shown in Table 4.

TABLE 4

Minimum inhibitory concentration of antimicrobial peptides against fungi

| | Candida albicans |
|---|---|
| XH-12C | 4 µM |
| XH-12B | 146 µM |
| XH-12A | 20 µM |

The experimental results showed that the above antimicrobial peptides, especially the antimicrobial peptides XH-12C and XH-12A, had inhibitory activities against Candida albicans.

Example 5 Determination of Inhibitory Activities and Half Maximal Inhibitory Concentration ($IC_{50}$) Against Drug-Resistant Cancer Cells The toxicity of antimicrobial peptides to cancer cells was analyzed by MTT assay. The cells were first digested with trypsin and suspended in a culture dish. The cell suspension was seeded in a 96-well plate at 180 µL per well to obtain a final concentration of $5 \times 10^3$ cells/well, and incubated for 24 hours. Different concentrations of peptide in each 20 µL were added, and topotecan, paclitaxel, vincristine and doxorubicin were used as positive controls. The plate was continuously incubated for 68 hours and added with 4 mg/mL of MTT reagent followed by another incubation for 4 hours. The supernatant was discarded and the crystallate was dissolved in 100 µL of DMSO for measurement of cell viability at 570 nm. The $IC_{50}$ value was calculated according to the survival curve. The experiment was repeated 3 times and the results were averaged and shown in Table 5.

TABLE 5

Minimum inhibitory concentration of antimicrobial peptides against cancer cells and drug-resistant cancer cells

| | H460 | MX20 | KB-3-1 | KB-C2 | KB-CV60 |
|---|---|---|---|---|---|
| XH-12C | 6 µM | 6 µM | 6 µM | 3 µM | 6 µM |
| XH-12B | 8 µM | 7 µM | 5 µM | 4 µM | 7 µM |
| XH-12A | 75 µM | 49 µM | 20 µM | 22 µM | 25 µM |

In Table 5, MX20 was a drug-resistant H460 cell strain overexpressing BCRP protein and induced by Mitoxantrone; KB-C2 was a drug-resistant KB-3-1 cell strain overexpressing P-gp protein and induced by Colchicine; and KB-CV60 was a drug-resistant KB-3-1 cellstrain overexpressing MRP1 protein and co-induced by Cepharanthine and Vincritine.

The experimental results showed that the above antimicrobial peptides had inhibitory activities against both cancer cells and drug-resistant cancer cells.

Example 6 Determination of Hemolytic Activity

1) Fresh human red blood cells were placed in a centrifuge tube containing heparin anticoagulant and centrifuged at 1,200 rpm for 15 minutes. The supernatant was discarded and the cells were washed several times with normal saline. The resulting red blood cells were prepared into a 2% (v/v) suspension with PBS. 100 µL of the cell suspension and 100 µL of an antimicrobial peptide solution (at a concentration of 16-3,200 µg/mL) were placed in a 96-well plate, incubated at 37° C. for 2 hours, centrifuged at 1,200 rpm for 10 minutes and measured at 620 nm by a microplate reader for the absorbance D. The hemolysis rate was calculated according to the equation: Hemolysis rate (%)=$(D_{test}-D_{negative})/(D_{positive}-D_{negative}) \times 100\%$. The experiment was repeated three times and the results were averaged. With reference to criteria for hemolysis test in the test methods of infusion equipment, transfusion equipment and injector for medical use, a hemolysis rate less than 5% indicated a negative reaction, i.e., the absence of hemolysis; and a hemolysis rate greater than 5% indicated a positive reaction, i.e., the occurrence of hemolysis. The results were shown in Table 6.

TABLE 6

Hemolytic activity of antimicrobial peptides for human red blood cells

| | Concentration for hemolysis rate less than 5% |
|---|---|
| XH-12C | 64 µg/mL |
| XH-12B | 80 µg/mL |
| XH-12A | 320 µg/mL |

The experimental results indicated no adverse effect of the above antimicrobial peptides on human red blood cells.

2) 6 mL of blood was collected from a heart of a healthy rabbit, immediately mixed with Alsever's solution in a ratio of 1:1, placed in a centrifuge tube and centrifuged at 1,200 rpm for 15 minutes. The supernatant was discarded and the cells were washed several times with normal saline. The resulting red blood cells were prepared into a 2% (v/v) suspension with PBS. 100 μL of the cell suspension and 100 μL of an antimicrobial peptide solution (at a concentration of 16-3200 μl g/mL) were placed in a 96-well plate, incubated at 37° C. for 2 hours, centrifuged at 1,200 rpm for 10 minutes and measured at 540 nm by a microplate reader for the absorbance D. The hemolysis rate was calculated according to the equation: Hemolysis rate (%)=($D_{test}$-$D_{negative}$)/($D_{positive}$-$D_{negative}$)×100%. The experiment was repeated three times and the results were averaged. With reference to criteria for hemolysis test in the test methods of infusion equipment, transfusion equipment and injector for medical use, a hemolysis rate less than 5% indicated a negative reaction, i.e., the absence of hemolysis; and a hemolysis rate greater than 5% indicated a positive reaction, i.e., the occurrence of hemolysis. The results were shown in Table 7.

TABLE 7

Hemolytic activity of antimicrobial peptides for rabbit red blood cells

| | Concentration for hemolysis rate less than 5% |
|---|---|
| XH-12C | 80 μg/mL |
| XH-12B | 160 μg/mL |
| XH-12A | 320 μg/mL |

The experimental results indicated no adverse effect of the above antimicrobial peptides on mammalian red blood cells.

Finally, it should also be noted that listed above are merely some embodiments of the invention. Obviously, the invention is not limited to the above embodiments and many variations of the embodiments can be made. All variations that can be directly derived or conceived by those skilled in the art from the disclosure of the invention should still fall within the scope of the invention.

We claim:

1. A method of treating an infection in a patient in need thereof, comprising:
   administering an antimicrobial peptide to the patient;
   wherein the antimicrobial peptide is selected from the group consisting of:
   XH-12C: Phe-Phe-Arg-Lys-Val-Leu-Lys-Leu-Ile-Arg-Lys-Ile-Trp-Arg shown as SEQ ID No.1;
   XH-12B: Phe-Phe-Arg-Lys-Val-Leu-Lys-Leu-Ile-Arg-Lys-Ile-Phe shown as SEQ ID No.2;
   XH-12A: Phe-Phe-Arg-Lys-Val-Leu-Lys-Leu-Ile-Arg-Lys-Ile shown as SEQ ID No.3; and a combination thereof;
   and the infection is caused by a fungus, a Gram-positive bacterium, a Gram-negative bacterium or a drug-resistant bacterium.

2. The method of claim 1, therein:
   the fungus is *Candida albicans*;
   the Gram-positive bacterium is selected from the group consisting of *Staphylococcus aureus* and *Listeria monocytogenes*;
   the Gram-negative bacterium is *Escherichia coli*; and
   the drug-resistant bacterium is selected from the group consisting of drug-resistant *Staphylococcus aureus*, drug-resistant *Acinetobacter baumannii*, drug-resistant *Klebsiella pneumoniae*, drug-resistant *Enterobacter sakazakii*, drug-resistant *Salmonella gallinarum*, drug-resistant *Streptococcus agalactiae*, drug-resistant *Enterococcus faecalis* and drug-resistant *Riemerella anatipestifer*.

* * * * *

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: The sequence is synthesized

<400> SEQUENCE: 1

Phe Phe Arg Lys Val Leu Lys Leu Ile Arg Lys Ile Trp Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: The sequence is synthesized

<400> SEQUENCE: 2

Phe Phe Arg Lys Val Leu Lys Leu Ile Arg Lys Ile Phe
1               5                   10

<210> SEQ ID NO 3
<211> LENGTH: 12
<212> TYPE: PRT
<213> ORGANISM: Artificial Sequence
<220> FEATURE:
<223> OTHER INFORMATION: The sequence is synthesized

<400> SEQUENCE: 3

Phe Phe Arg Lys Val Leu Lys Leu Ile Arg Lys Ile
1               5                   10
```